(12) United States Patent
Hirayama et al.

(10) Patent No.: US 10,799,089 B2
(45) Date of Patent: Oct. 13, 2020

(54) OBSERVATION DEVICE AND OBSERVATION SYSTEM FOR STRENGTHENING STABILITY OF COMMUNICATION

(71) Applicant: SONY CORPORATION, Tokyo (JP)

(72) Inventors: Tomoyuki Hirayama, Kanagawa (JP); Hiroshi Ichiki, Kanagawa (JP); Masahito Yamane, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 524 days.

(21) Appl. No.: 15/522,142

(22) PCT Filed: Sep. 8, 2015

(86) PCT No.: PCT/JP2015/075485
§ 371 (c)(1),
(2) Date: Apr. 26, 2017

(87) PCT Pub. No.: WO2016/072147
PCT Pub. Date: May 12, 2016

(65) Prior Publication Data
US 2017/0311777 A1    Nov. 2, 2017

(30) Foreign Application Priority Data
Nov. 7, 2014   (JP) .................................. 2014-227281

(51) Int. Cl.
*A61B 1/00*    (2006.01)
*A61B 1/04*    (2006.01)
(Continued)

(52) U.S. Cl.
CPC ...... *A61B 1/00016* (2013.01); *A61B 1/00006* (2013.01); *A61B 1/00009* (2013.01);
(Continued)

(58) Field of Classification Search
CPC combination set(s) only.
See application file for complete search history.

(56) References Cited

U.S. PATENT DOCUMENTS

| 2002/0067408 A1* | 6/2002 | Adair ................ A61B 1/00016 348/76 |
| 2008/0318540 A1* | 12/2008 | Homan ............ A61B 1/00016 455/277.1 |

(Continued)

FOREIGN PATENT DOCUMENTS

| JP | 2001-275950 A | 10/2001 |
| JP | 2005-021516 A | 1/2005 |

(Continued)

OTHER PUBLICATIONS

International Search Report and Written Opinion of PCT Application No. PCT/JP2015/075485, dated Dec. 15, 2015, 06 pages of English Translation and 06 pages of ISRWO.

(Continued)

*Primary Examiner* — John P Leubecker
*Assistant Examiner* — Shankar Raj Ghimire
(74) *Attorney, Agent, or Firm* — Chip Law Group (57) ABSTRACT

There is provided an observation device that includes an image shooting unit composed of a first housing and for capturing an image of a surgical site of a patient; and a communication unit composed of a second housing disposed away from the first housing, and for wirelessly transmitting, to an external device, image information on the surgical site the image of which is captured by the image shooting unit.

13 Claims, 7 Drawing Sheets

(51) Int. Cl.
*A61B 1/06* (2006.01)
*A61B 1/313* (2006.01)

(52) U.S. Cl.
CPC ...... *A61B 1/00018* (2013.01); *A61B 1/00032* (2013.01); *A61B 1/00045* (2013.01); *A61B 1/00133* (2013.01); *A61B 1/04* (2013.01); *A61B 1/0661* (2013.01); *A61B 1/313* (2013.01)

(56) References Cited

U.S. PATENT DOCUMENTS

| | | | | |
|---|---|---|---|---|
| 2009/0171146 | A1* | 7/2009 | Fujita | A61B 1/00158 600/102 |
| 2009/0203964 | A1 | 8/2009 | Shimizu et al. | |
| 2009/0300507 | A1* | 12/2009 | Raghavan | G06F 19/3418 715/738 |
| 2010/0280340 | A1* | 11/2010 | Homan | A61B 1/00016 600/302 |
| 2013/0060914 | A1* | 3/2013 | Callahan | G06Q 30/02 709/219 |
| 2014/0114196 | A1* | 4/2014 | Kamimura | A61B 1/00167 600/478 |
| 2014/0171789 | A1* | 6/2014 | Barth | A61B 5/062 600/424 |
| 2014/0276056 | A1* | 9/2014 | Ohta | A61B 6/465 600/440 |
| 2015/0297062 | A1* | 10/2015 | Golenberg | A61B 1/00006 348/68 |
| 2017/0273549 | A1* | 9/2017 | Nazareth | A61B 1/04 |

FOREIGN PATENT DOCUMENTS

| | | |
|---|---|---|
| JP | 2005-21516 A | 1/2005 |
| JP | 2007-061296 A | 3/2007 |
| JP | 2007-61296 A | 3/2007 |
| JP | 2009-189475 A | 8/2009 |
| JP | 2010-509990 A | 4/2010 |
| JP | 2010-187729 A | 9/2010 |
| JP | 2013-183948 A | 9/2013 |

OTHER PUBLICATIONS

International Preliminary Report on Patentability of PCT Application No. PCT/JP2015/075485, dated May 18, 2017, 07 pages of English Translation and 03 pages of IPRP.

* cited by examiner

OBSERVATION DEVICE AND OBSERVATION SYSTEM FOR STRENGTHENING STABILITY OF COMMUNICATION

CROSS REFERENCE TO RELATED APPLICATIONS

This application is a U.S. National Phase of International Patent Application No. PCT/JP2015/075485 filed on Sep. 8, 2015, which claims priority benefit of Japanese Patent Application No. JP 2014-227281 filed in the Japan Patent Office on Nov. 7, 2014. Each of the above-referenced applications is hereby incorporated herein by reference in its entirety.

TECHNICAL FIELD

The present disclosure relates to an observation device and an observation system.

BACKGROUND ART

There is a widely used system that uses an observation device such as an endoscope or a microscope to capture an image of a surgical site of a patient, and allows a surgeon to perform an operation while observing the captured image. The system transmits information on the image captured by the observation device to a processor (video processor) that performs display control of the image, and causes the video processor to display the image on a display device such as a monitor in an operating room. It is required to further strengthen the stability of the communication between the observation device and the video processor to prevent the image from breaking off during an operation.

Generally, the communication between the observation device and the video processor for transmitting and receiving image information is wired communication in many cases. However, in a case where wired communication is used, the observation device in a clean area is connected to the video processor in an unclean area by a cable or the like. Accordingly, more attention has to be paid to maintain the clean area. Further, a heavy load is imposed to sterilize the cable. Moreover, the installation of the cable on the floor can interfere with a medical staff moving in the operating room. Further, there is a concern that the presence of the cable imposes a heavier load on a doctor who operates the observation device. Moreover, the cable can interfere with the field of view of a surgeon watching the display device.

There is then developed a technique that connects an endoscope to a video processor through wireless communication (e.g., Patent Literature 1). The technique described in Patent Literature 1 devises the position for disposing an antenna in the endoscope, thereby making it possible to more stably perform communication, and to acquire an image having higher quality.

CITATION LIST

Patent Literature

Patent Literature 1: JP 2010-509990T

DISCLOSURE OF INVENTION

Technical Problem

The operating room is, however, dotted with a large medical staff, a variety of medical devices, support tables (Mayo tables) on which instruments used for operations are placed, and the like. If these people and objects enter the communication path between the observation device and the video processor, the normal communication can be interrupted between the observation device and the video processor. The technique described in Patent Literature 1 does not take into consideration the influence of these people and objects in the operation room on the communication. The stable communication is not always ensured.

The present disclosure then proposes a novel and improved observation device and observation system that can more stably perform communication.

Solution to Problem

According to the present disclosure, there is provided an observation device including: an image shooting unit composed of a first housing and configured to capture an image of a surgical site of a patient; and a communication unit composed of a second housing disposed away from the first housing, and configured to wirelessly transmit, to an external device, image information on the surgical site the image of which is captured by the image shooting unit.

Further, according to the present disclosure, there is provided an observation system including: an observation device configured to wirelessly transmit image information on a surgical site of a patient; and a display control device configured to receive the image information transmitted from the observation device, and to control display of an image on the surgical site. The observation device includes an image shooting unit composed of a first housing and configured to capture an image of the surgical site of the patient, and a communication unit composed of a second housing disposed away from the first housing, and configured to wirelessly transmit, to the display control device, the image information on the surgical site the image of which is captured by the image shooting unit.

According to the present disclosure, an observation device includes an image shooting unit and a communication unit that are composed of different housings. This thus improves the flexibility of the position for disposing the communication unit, in particular, the position for disposing an antenna of the communication unit that wirelessly transmits, to an external device (display control device), image information on a surgical site an image of which is captured by the image shooting unit. The antenna can be hereby disposed at a position at which radio waves are more difficult to block and communication can be stably performed, which can further strengthen the stability of the communication between the observation device and the display control device.

Advantageous Effects of Invention

As described above, according to the present disclosure, it is possible to more stably perform communication. Note that the effects described above are not necessarily limitative. With or in the place of the above effects, there may be achieved any one of the effects described in this specification or other effects that may be grasped from this specification.

MODE(S) FOR CARRYING OUT THE INVENTION

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be now made in the following order.
1. Configuration of Observation System
2. Functional Configuration of Observation System
3. Modifications
3-1. Modification of Connection between Image Shooting Unit and Communication Unit
3-2. Modification of Position for Disposing Transmitting and Receiving Section of Communication Unit
4. Supplemental Information

1. Configuration of Observation System

Figure 1:
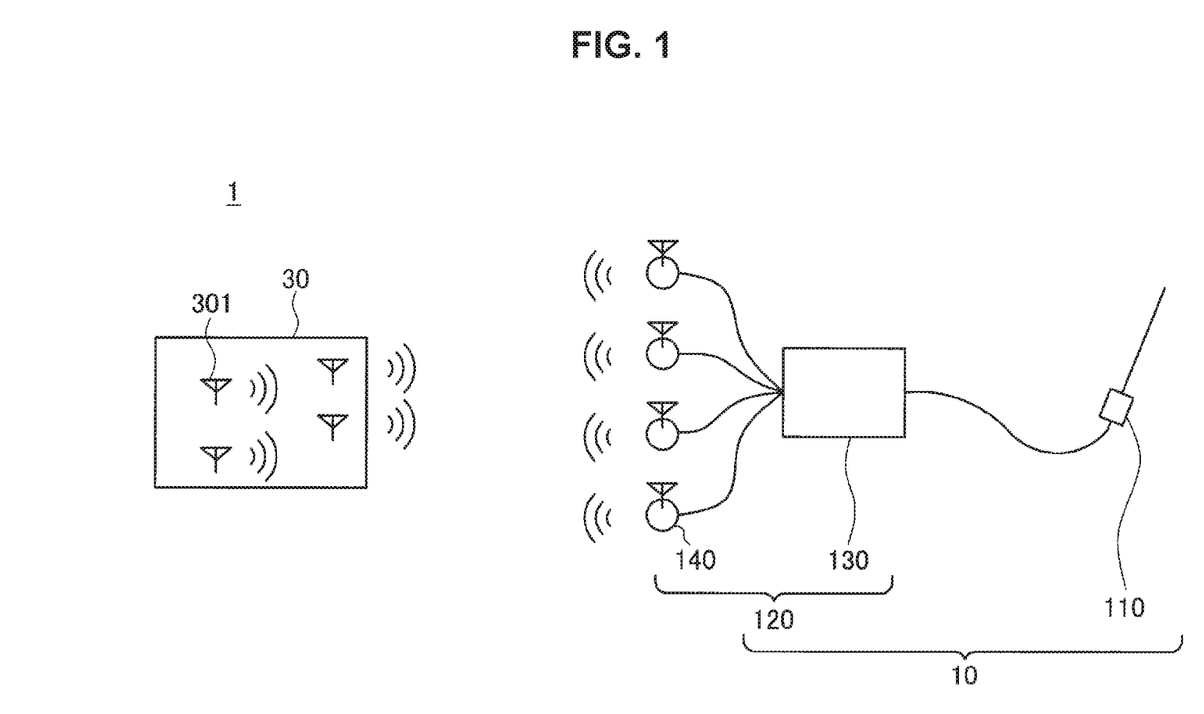
FIG. 1 is a diagram illustrating a schematic configuration of an observation system according to an embodiment of the present disclosure.
Figure 2:
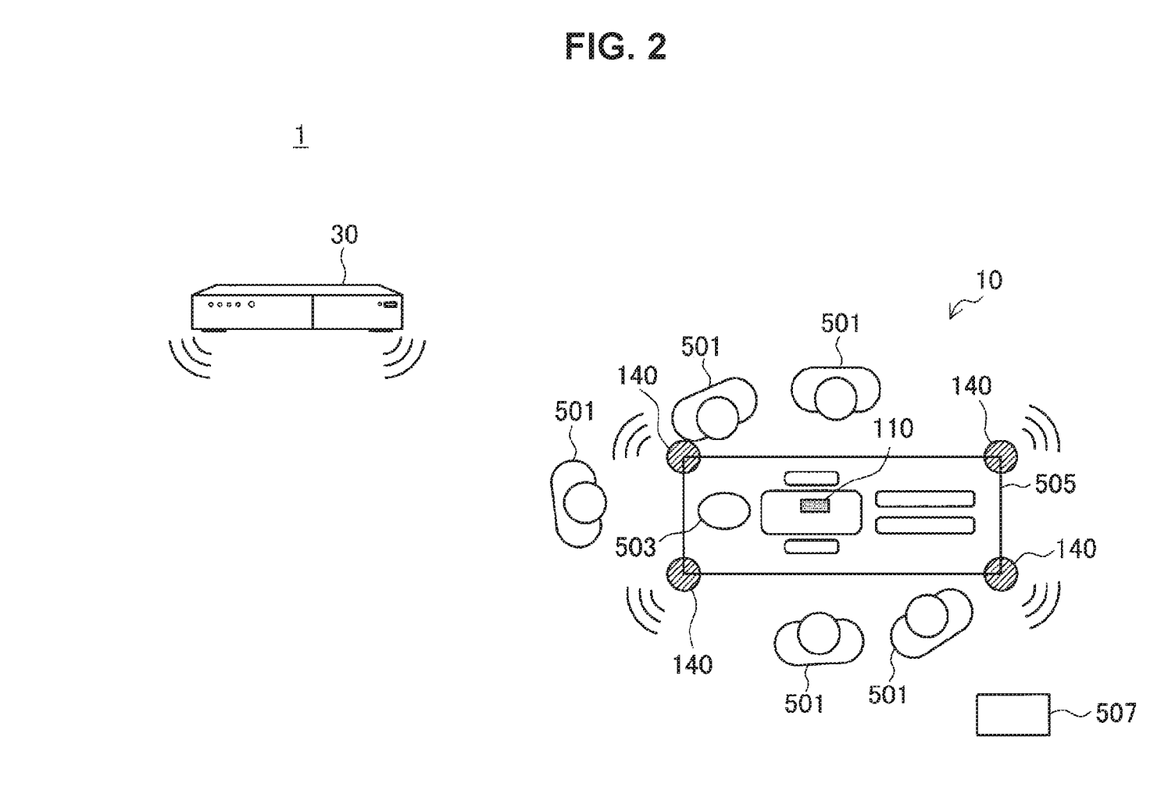
FIG. 2 is a diagram illustrating a more detailed configuration of the observation system according to the present embodiment.
Figure 3:
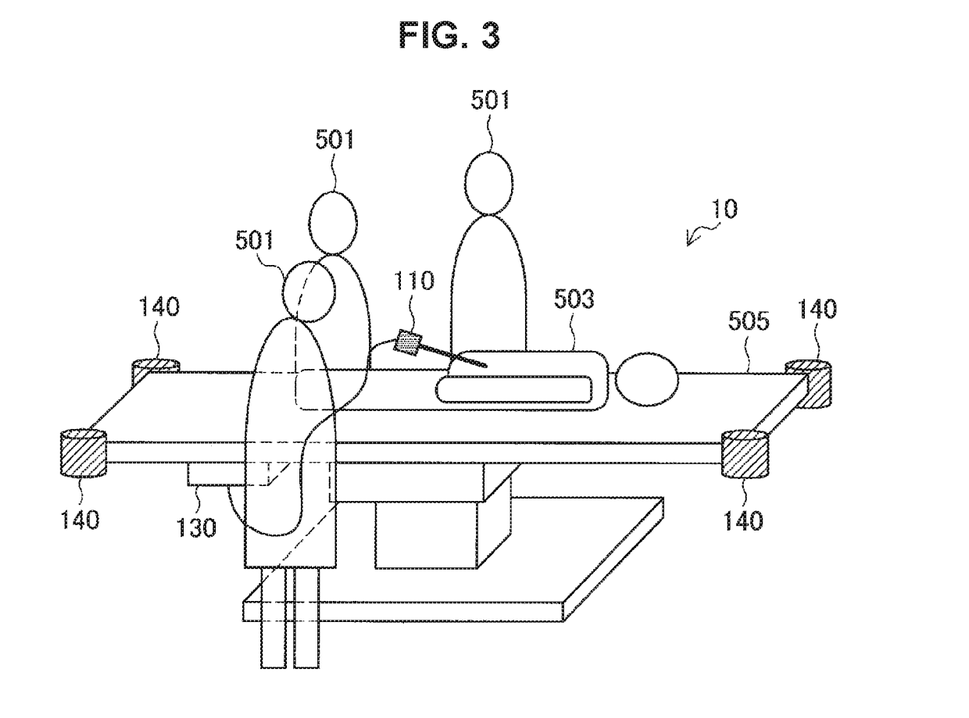
FIG. 3 is a diagram for describing a position for disposing a communication unit illustrated in FIGS. 1 and 2.
Figure 4:
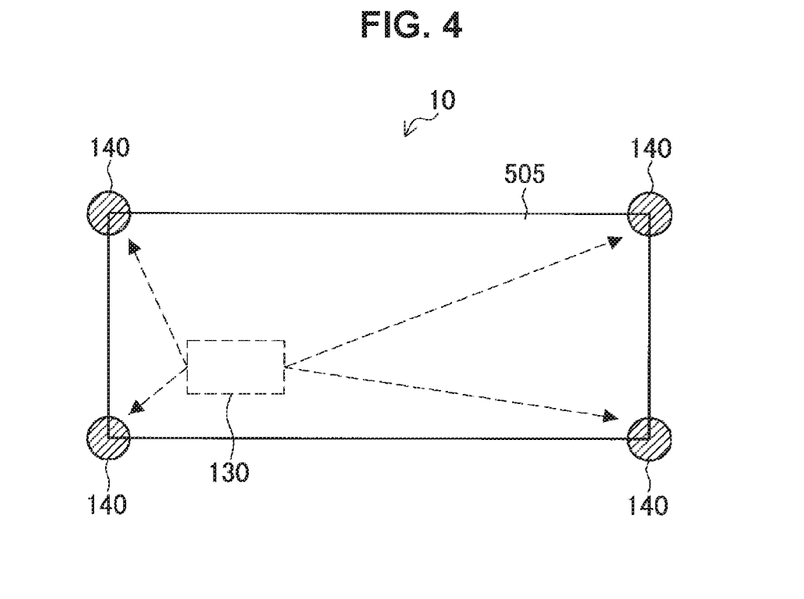
FIG. 4 is a diagram for describing the position for disposing the communication unit illustrated in FIGS. 1 and 2.
Figure 5:
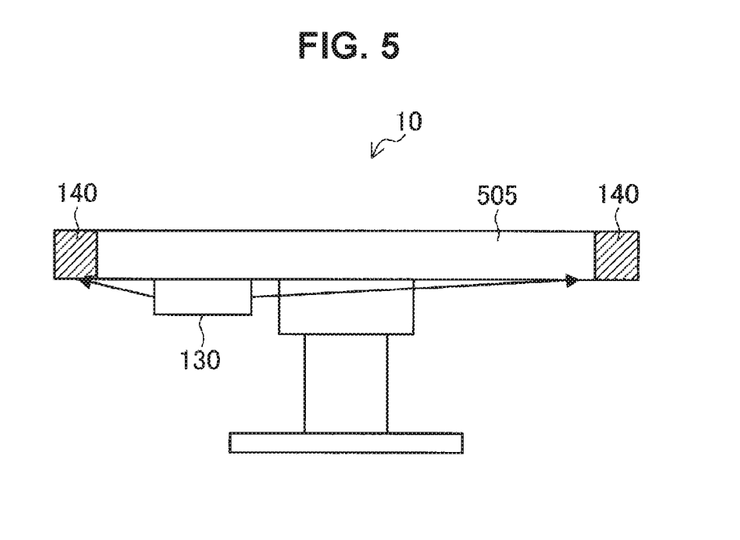
FIG. 5 is a diagram for describing the position for disposing the communication unit illustrated in FIGS. 1 and 2.

The configuration of an observation system according to an embodiment of the present disclosure will be described with reference to FIGS. 1 to 5. FIG. 1 is a diagram illustrating the schematic configuration of the observation system according to the embodiment of the present disclosure. FIG. 2 is a diagram illustrating the more detailed configuration of the observation system according to the present embodiment. Each of FIGS. 3 to 5 is a diagram for describing the position for disposing a communication unit illustrated in FIGS. 1 and 2.

Additionally, the following describes, as an example of the present embodiment, a case where the observation device that observes a surgical site of a patient is an endoscope. The present embodiment is not, however, limited to the example. The observation device may be another device such as a microscope (operating microscope) for observing a surgical site.

FIG. 1 illustrates that an observation system 1 according to the present embodiment includes an endoscope 10 and a video processor 30.

The endoscope 10 is an example of an observation device that observes a surgical site of a patient. The endoscope 10 includes an image shooting unit 110 composed of a first housing, and a communication unit 120 composed of a second housing different from the first housing. The image shooting unit 110 and the communication unit 120 are connected to each other by a cable, and can transmit and receive various kinds of information to and from each other through wired communication.

The image shooting unit 110 captures an image of a surgical site (surgical site image). The image shooting unit 110 includes, in a lens barrel, a light source that irradiates a surgical site, an image sensor that captures an image of the surgical site by detecting the reflected light of the radiated light, and the like. The lens barrel of the image shooting unit 110 is inserted into a body cavity of a patient, for example, through an incision of the skin, and captures an image of the condition of a surgical site in the body cavity. Information on the image of the surgical site captured by the image shooting unit 110 (surgical site image information) is transmitted to the communication unit 120 through wired communication via a cable.

The communication unit 120 has a function of wirelessly transmitting the information on the image of the surgical site captured by the image shooting unit 110 to the video processor 30. Further, the communication unit 120 additionally has a control function of integrally controlling the operations of the endoscope 10 such as the image shooting unit 110 capturing an image of a surgical site and wirelessly transmitting surgical site image information to the video processor 30.

More specifically, the communication unit 120 includes a main body section 130 and transmitting and receiving sections 140 that are connected to each other by cables to allow for wired communication. The main body section 130 includes a variety of processing circuits such as a central processing unit (CPU), a digital signal processor (DSP) and a graphics processing unit (GPU), a power source section (battery) that supplies driving power to the processing circuits and the image shooting unit 110, and the like. The processing circuits operate in accordance with predetermined programs, thereby controlling the variety of operations of the endoscope 10. Further, the transmitting and receiving sections 140 each include an antenna for wirelessly transmitting and receiving surgical site image information.

The image shooting unit 110 is controlled by the main body section 130 of the communication unit 120 to capture an image of a surgical site. Information on the surgical site image captured by the image shooting unit 110 is transmitted to the main body section 130 of the communication unit 120 via a cable in a wired manner. The communication unit 120 is controlled by the main body section 130 to wirelessly transmit the information on the surgical site image captured by the image shooting unit 110 to the video processor 30 via the transmitting and receiving sections 140.

The video processor 30 is an example of a display device that performs control to display a surgical site image captured by the endoscope 10 on the display device. Although not illustrated, the video processor 30 includes an antenna for receiving the surgical site image information. The video processor 30 includes a variety of processing circuits such as a CPU, a DSP, and a GPU. These processing circuits operate in accordance with predetermined programs to realize the functions of the video processor.

The video processor 30 may have a variety of functions of a general display control device. For example, the video processor 30 may have a function of performing general image processing on image information such as adjusting brightness and luminance. The video processor 30 may also perform various kinds of image processing on surgical site image information transmitted from the endoscope 10, and then display the surgical site image on the display device. Further, the video processor 30 may additionally have a function of wirelessly controlling the driving of the light source and the image sensor of the image shooting unit 110. For example, the video processor 30 may control the analog gain or the like of the image sensor of the image shooting unit 110 as appropriate to adjust the overall brightness of the surgical site image.

Here, as described below, surgical site image information that is subjected to a compression process and has the reduced amount of data is transmitted from the endoscope 10 to the video processor 30 in the present embodiment. Thus, even in a case where the endoscope 10 captures an image having high resolution, the wireless communication between the endoscope 10 and the video processor 30 is not required to be so fast. Radio waves having, for example, a relatively low frequency band of some GHz can be used. Radio waves having a lower frequency band have a weaker property of traveling straight than that of radio waves having a higher frequency band of some 60 GHz, which are referred to, for example, as millimeter waves. Accordingly, even in a case where there is an obstacle between the antennas of devices on a communication path, the radio waves can propagate between the antennas by diffracting around the obstacle. More stable communication can be thus realized.

A variety of known communication standards may be used for the standard of wireless communication that uses radio waves of a lower frequency band. For example, Miracast (registered trademark), WiDi (registered trademark), AirPlay (registered trademark), a variety of communication standards that use the ultra wide band (UWB) scheme, WHDI (registered trademark), or the like can be used for wireless communication for transferring image information with a lower frequency band. Further, not limited to the transfer use of image information, what complies with the respective standards such as IEEE 802.11b/a/g/j/n/ac, TransferJet (registered trademark), or the like may be used for wireless communication that uses radio waves of a lower frequency band.

Additionally, a communication path means a path for transmitting surgical site image information between the endoscope 10 and the video processor 30 in the present embodiment. Specifically, the communication path is a path connecting each of the transmitting and receiving sections 140 (i.e., antennas) of the endoscope 10 to the antenna of the video processor 30. In a case where there is an object on a communication path, the object can block the radio waves or interfere with the communication. This tendency can be remarkable in wireless communication that uses radio waves of a relatively high frequency band such as millimeter waves. This is because radio waves of high frequency bands such as millimeter waves are known to have the strong property of traveling straight.

Here, as described above, the endoscope 10 includes the image shooting unit 110 and the communication unit 120 that are connected to each other by a cable in the present embodiment. Moreover, the communication unit 120 includes a main body section 130 and transmitting and receiving sections 140 that are connected to each other by cables. It is thus possible to dispose the transmitting and receiving sections 140, namely the antennas at freer positions. The flexibility of the positions for disposing the transmitting and receiving sections 140 is improved, thereby making it possible to further strengthen the stability of the communication between the endoscope 10 and the video processor 30.

An example of the positions for disposing the transmitting and receiving sections 140 in a case where the observation system 1 illustrated in FIG. 1 is actually installed in an operating room will be described with reference to FIGS. 2 to 5. FIG. 2 illustrates an overhead view of a configuration example of the observation system 1 illustrated in FIG. 1 and actually installed in an operating room.

FIG. 2 illustrates that a patient 503 lies down on an operating table 505. The operating table 505 is surrounded by a medical staff 501 such as doctors and nurses. The place of the medical staff 501 move as needed during an operation.

The operating table 505 is further surrounded by other objects such as a Mayo table 507 on which surgical instruments are placed. Further, although not illustrated, the operating table 505 can be surrounded by a variety of medical devices such as a measurement device used for an operation to measure the vital signs of a patient. The places of the Mayo table 507 and these medical devices can also be moved as needed during an operation. Objects such as the medical staff 501 and the Mayo table 507 can block the radio waves between the endoscope 10 and the video processor 30 in an operating room, and obstruct the communication.

The lens barrel of the image shooting unit 110 of the endoscope 10 is inserted into a body cavity of the patient 503, and the image shooting unit 110 captures an image of a surgical site in the body cavity in an endoscopic operation. The image shooting unit 110 is held by a medical specialist referred to as scopist during an operation.

FIGS. 3 to 5 respectively illustrate an oblique top view, top view, and side view of the operating table 505 illustrated in FIG. 2. FIGS. 3 to 5 omit some of the people and the objects illustrated in FIG. 2 to illustrate the positions for disposing the main body section 130 and the transmitting and receiving sections 140 of the communication unit 120.

As illustrated in FIGS. 2 to 5, the main body section 130 of the communication unit 120 is favorably installed on the bottom of the operating table 505 in the present embodiment. Further, the transmitting and receiving sections 140 of the communication unit 120 are favorably installed at the respective four corners of the operating table 505. Although not illustrated in FIGS. 2 and 3 for the sake of simplicity, the main body section 130 and the transmitting and receiving sections 140 are actually connected to each other by cables. FIGS. 4 and 5 simulatively illustrate the cables connecting the main body section 130 and the transmitting and receiving sections 140 as arrows.

Here, for example, the general existing endoscope as described in Patent Literature 1 includes an image shooting unit and a communication unit that are integrated with each other. Thus, the general endoscope also includes an antenna for transmitting a surgical site image at the position of the image shooting unit 110 illustrated in FIG. 2, and surgical site image information is transmitted to the video processor 30 from this position.

Here, members of the medical staff 501 perform various kinds of treatment on a surgical site of a patient. Accordingly, other members of the medical staff 501, not to mention a scopist, and instruments such as the Mayo table 507 relatively densely surround the surgical site. Thus, in a case where an antenna for transmitting a surgical site image is positioned near a surgical site of a patient like the general endoscope, there is a high probability that obstacles such as the medical staff 501 and the Mayo table 507 interfere with the communication.

Further, the overall configuration of the endoscope is generally required to be smaller and lighter from the perspective of the operability of a scopist. There is thus a restriction on components that can be installed in the endoscope. For example, it is difficult to install a big battery therein.

Meanwhile, the endoscope 10 separately includes the image shooting unit 110 and the communication unit 120 that are composed of different housings in the present embodiment. Moreover, the communication unit 120 also separately includes the main body section 130 and the transmitting and receiving sections 140.

This thus improves the flexibility of the positions for disposing the transmitting and receiving sections 140. For example, as described above, it is possible to install the transmitting and receiving sections 140 at positions distant from a surgical site, such as the four corners of the operating table 505. Disposing the transmitting and receiving sections 140 at positions distant from a surgical site makes it less likely that the communication paths from the transmitting and receiving sections 140 to the video processor 30 are blocked by obstacles such as the medical staff 501 and the Mayo table 507. The stability of the wireless communication between the endoscope 10 and the video processor 30 can be strengthened.

Further, since the endoscope 10 separately includes the image shooting unit 110 and the communication unit 120, a scopist only has to operate the image shooting unit 110 alone. The load on the scopist is then reduced. Further, for example, as described above, the main body section 130 can be installed at a position such as the bottom of the operating table 505 which has no influence on the operation of the medical staff 501. Even in a case where the main body section 130 is bigger, the main body section 130 does not thus reduce the operability of a scopist, or interrupt another member of the medical staff. It is thus possible to improve the flexibility of members that are installed in the main body section 130 such as installing a power source section having large capacity.

The configuration of the observation system 1 according to the present embodiment has been described above with reference to FIGS. 1 to 5.

2. Functional Configuration of Observation System

Figure 6:
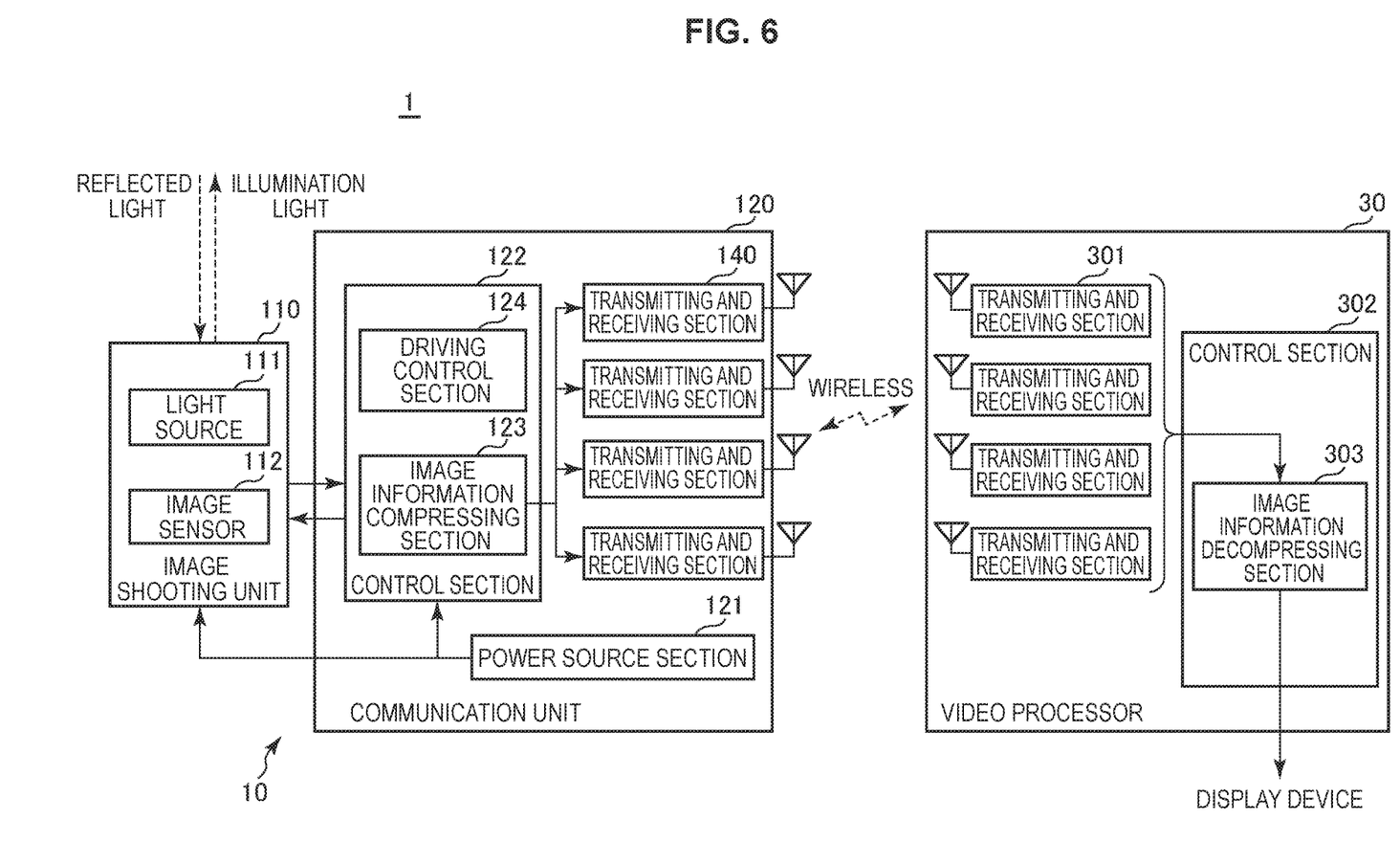
FIG. 6 is a functional block diagram illustrating an example of a functional configuration of the observation system according to the present embodiment.

The functional configuration of the observation system 1 according to the present embodiment will be described with reference to FIG. 6. FIG. 6 is a functional block diagram illustrating an example of the functional configuration of the observation system 1 according to the present embodiment. FIG. 6 corresponds to the illustration showing the functions of each device in the observation system 1 illustrated in FIGS. 1 and 2 as functional blocks.

FIG. 6 illustrates that the observation system 1 according to the present embodiment includes the endoscope 10 and the video processor 30 that are connected to allow for wireless communication. Further, the endoscope 10 includes the image shooting unit 110 and the communication unit 120 that are composed of different housings and connected to each other to allow for wired communication.

The image shooting unit 110 includes a light source 111 and an image sensor 112. The light source 111 and the image sensor 112 are disposed in a lens barrel. The light source 111 and the image sensor 112 are provided, for example, at positions such as the tip of the lens barrel which faces a surgical site of a patient when the lens barrel is inserted into a body cavity of the patient.

The light source 111 irradiates a surgical site with light. A variety of light sources used for the general existing endoscope may be used as the light source 111. The light source 111 may be, for example, a light emitting diode (LED), a laser light source, or the like. The driving of the light source 111 is controlled by the following control section 122 of the communication unit 120.

The image sensor 112 captures an image of a surgical site by detecting the reflected light of the light with which the light source 111 irradiates the surgical site. A variety of image sensors used for the general existing endoscope may be used as the image sensor 112. The image sensor 112 may be, for example, a charge coupled device (CCD) image sensor, a complementary metal-oxide-semiconductor (CMOS) image sensor, or the like.

The driving of the image sensor 112 is controlled by the following control section 122 of the communication unit 120. Further, information on a surgical site image captured by the image sensor 112 is transmitted to the following control section 122 of the communication unit 120 through wired communication.

The communication unit 120 includes a power source section 121, the control section 122, and the transmitting and receiving sections 140 as functions thereof. The components corresponding to the power source section 121 and the control section 122 among those functions can be integrated with the above-described main body section 130. Further, the transmitting and receiving sections 140 correspond to the transmitting and receiving sections 140 illustrated in FIGS. 1 to 5. The transmitting and receiving sections 140 include antennas for wireless communication. In this way, although not explicitly illustrated in FIG. 6, the communication unit 120 includes the main body section and the transmitting and receiving sections 140 that are connected to each other by cables. The main body section includes the components corresponding to the power source section 121 and the control section 122.

The power source section 121 supplies driving power to each member of the endoscope 10. The power source section 121 can include a variety of batteries. As illustrated, the power source section 121 can supply power to the image shooting unit 110 and the control section 122.

Here, the endoscope 10 separately includes the image shooting unit 110 and the communication unit 120 as described above in the present embodiment. Thus, even if the main body section of the communication unit 120 is bigger, it is possible to dispose the main body section at a position at which the main body section has no influence on the operability of a doctor (scopist) operating the image shooting unit 110 or the performance of an operation. It is thus possible to use a battery having larger capacity as a battery included in the power source section 121.

The control section 122 includes a variety of processing circuits such as a CPU, a DSP, and a GPU, and integrally controls the operation of the endoscope 10. The processing circuits included in the control section 122 operate in accordance with predetermined programs, thereby realizing the respective functions of the control section 122.

The control section 122 includes an image information compressing section 123 and a drive control section 124 as functions thereof.

The image information compressing section 123 performs a compression process on information on a surgical site image captured by the image shooting unit 110, and compresses the surgical site image information into a smaller amount of data. The control section 122 emits the surgical site image information compressed by the image information compressing section 123 to the space via the transmitting and receiving sections 140.

Here, the image information compressing section 123 compresses the surgical site image information by a method that causes so little delay in the present embodiment that, when the compressed surgical site image information is transmitted to the video processor 30 and the surgical site image is displayed on the display device, the performance of a medical staff performing an operation while watching the surgical site image is not affected. A variety of known methods may be used as such a method for a compression process with little delay. The details will not be then described here.

The drive control section 124 controls the driving of the image shooting unit 110, and captures an image of a surgical site. Specifically, the drive control section 124 controls the driving of the light source 111 and the image sensor 112 of the image shooting unit 110 as appropriate on the basis of an image capturing condition set as appropriate by a user such as a surgeon, thereby capturing an image of a surgical site under the desired image capturing condition. For example, the drive control section 124 may change the setting such as an analog gain of the image sensor 112 as appropriate in accordance with an image capturing condition. Further, for example, in a case where the light source 111 has a function of switching the wavelength band of radiated light, the drive control section 124 may perform control to switch the light radiated from the light source 111, for example, between white light for general observation and light of a predetermined wavelength band for fluorescence observation of an affected region such as a tumor in accordance with the purpose of observation. Additionally, in a case where the video processor 30 has a function of controlling the driving of the image shooting unit 110, the drive control section 124 may control the driving of the image shooting unit 110 in accordance with an instruction from the video processor 30.

The video processor 30 includes transmitting and receiving sections 301 and a control section 302 as functions thereof.

The transmitting and receiving sections 301 include antennas for receiving surgical site image information wirelessly transmitted from the endoscope 10. The video processor 30 may include the transmitting and receiving sections 301 provided at different positions in the housing. The video processor 30 can select, as appropriate, the transmitting and receiving section 301 from the transmitting and receiving sections 301 which can perform more preferred communication in accordance with the positional relationship between the transmitting and receiving sections 301 and the transmitting and receiving sections 140 of the endoscope 10, and receive the surgical site image information. The surgical site image information received by any of the transmitting and receiving sections 301 is provided to the control section 302. In other words, the control section 302 selects the channel corresponding to the more appropriate transmitting and receiving section 301 for receiving surgical site image information, and acquires the surgical site image information.

The surgical site image information compressed by the image information compressing section 123 is transmitted from the endoscope 10 to the video processor 30 in the present embodiment. Thus, even in a case where the endoscope 10 captures an image having high resolution, it is possible to keep the amount of data to be transmitted relatively small. It is thus possible to use radio waves of the above-described relatively low frequency band for the wireless communication between the endoscope 10 and the video processor 30.

The control section 302 includes a variety of processing circuits such as a CPU, a DSP, and a GPU, and integrally controls the operation of the video processor 30. The processing circuits included in the control section 302 operate in accordance with predetermined programs, thereby realizing the respective functions of the control section 302.

The control section 302 includes an image information decompressing section 303 as a function thereof. Although not illustrated, the control section 302 may additionally have a variety of functions of the general display control device such as performing various kinds of image processing on image information, and displaying the image information on the display device. Further, the control section 302 may additionally have a function of controlling the driving of the image shooting unit 110. In that case, an instruction from the control section 302 is transmitted to the drive control section 124 of the control section 122 of the communication unit 120 through wireless communication. The control section 302 can hereby control the driving of the image shooting unit 110 via the drive control section 124.

The image information decompressing section 303 performs a decompression process on operating room image information acquired via the transmitting and receiving sections 301. The image information decompressing section 303, however, decompresses the surgical site image information by a method with relatively little delay in the present embodiment. A method of the image information decompressing section 303 for a decompression process on data may correspond to a method of the image information compressing section 123 of the control section 122 of the communication unit 120 for a compression process on data. A variety of known methods may be used as the method for a decompression process. The details will not be then described here.

The surgical site image information decompressed by the image information decompressing section 303 is subjected, for example, to various kinds of image processing, and then displayed on the display device provided in an operating room.

The functional configuration of the observation system 1 according to the present embodiment has been described above with reference to FIG. 6. As described above, according to the present embodiment, the endoscope 10 separately includes the image shooting unit 110 and the communication unit 120. Moreover, the communication unit 120 also separately includes the main body section 130 and the transmitting and receiving sections 140. The main body section 130 of the communication unit 120 can be thus disposed at a position different from the position of the image shooting unit 110. Even if the main body section 130 is bigger, the main body section 130 does not then interrupt the operation of a scopist or another member of the medical staff. Accordingly, it is possible to use a battery having larger capacity as the power source section 121 installed in the main body section 130. Thus, even in a case where the control section 122 includes a high-performance processing circuit capable of executing a heavy-load process such as the compression process with little delay performed by the image information compressing section 123, it is possible to supply the power for the consumed power from the power source section 121.

In this way, the communication unit 120 of the endoscope 10 separately includes the main body section 130 and the transmitting and receiving sections 140 in the present embodiment. It is hereby possible to perform a compression process with little delay without increasing the load on a scopist, and to perform more stable wireless communication of a low frequency band for surgical site image information. Even in a case where there is an obstacle on the communication paths from the transmitting and receiving sections 140 to the video processor 30, performing wireless communication by using radio waves of a low frequency band prevents the obstacle from hindering the communication, and makes it possible to more stably perform the wireless communication between the endoscope 10 and the video processor 30.

Here, for example, in a case where information having a large amount of data is wirelessly transmitted, it is necessary to use radio waves of a relatively high frequency band such as millimeter waves for fast communication. Radio waves of a high frequency band such as millimeter waves are known to have the strong property of traveling straight. For example, in a case where there is an obstacle in a communication path, there is a high probability that the radio waves are blocked by the obstacle. In this way, there is a concern that communication using radio waves of a high frequency band has weakened stability.

Further, it is difficult unlike the present embodiment, for example, for the general endoscope including an image shooting unit and a communication unit that are integrated with each other as described in Patent Literature 1 to perform a compression process with little delay on surgical site image information, and then transmit the surgical site image information to a video processor. This is because the endoscope has to be bigger owing to the necessity of a battery sufficient for the power consumed by a relatively high-performance processing circuit which performs a compression process with little delay at higher processing speed. The bigger endoscope is not favorable because the bigger endoscope decreases the operability of a scopist.

Meanwhile, according to the present embodiment, the communication unit 120 of the endoscope 10 separately includes the main body section 130 and the transmitting and receiving sections 140 as described above. It is hereby possible to perform a compression process with little delay without increasing the load on a scopist, and to perform more stable wireless communication of a low frequency band for surgical site image information. It is thus possible to perform more stable wireless communication between the endoscope 10 and the video processor 30 than communication that uses radio waves of a high frequency band. Here, the observation system 1 has to prevent the communication between the endoscope 10 and the video processor 30 from being unstable, and a distorted surgical site image from being displayed on the display device during an operation. This is because a serious accident can happen if a distorted surgical site image or a disrupted surgical site image causes an operation to stop. It is possible in the present embodiment to strengthen the stability of communication without causing delay in displaying surgical site image, and to prevent a distorted surgical site image from being displayed, by transmitting, in radio waves of a low frequency band, surgical site image information compressed with little delay.

Further, since more stable wireless communication is realized between the endoscope 10 and the video processor 30 in this way according to the present embodiment, there is no need to perform wired communication between the endoscope 10 and the video processor 30 by using a cable. Cables are dispensable between the endoscope 10 and the video processor 30. It is thus possible to reduce the load on a scopist, securing a surgeon a wider field of view. Further, the efficiency and safety of an operation are accordingly improved. Further, the absence of a cable makes it easier to maintain a clean area, and to reduce the load for sterilizing the cable. Moreover, the movement of the medical staff is not interrupted by the cable laid on the floor. Neither does the endoscope 10 shaken by accidental contact with the cable on the floor cause a surgical site image to blur. Accordingly, the efficiency and safety of an operation are improved.

The main body section 130 does not have to necessarily include the power source section 121 in the present embodiment. For example, in a case where the operating table 505 illustrated in FIG. 2 is an electrically-powered operating table, the operating table 505 includes a battery or is supplied with power from an external power source (such as an electrical outlet). The main body section 130 does not have to include the power source section 121, but the main body section 130 may be supplied with power from the operating table 505 in the present embodiment. Even in this case, since the endoscope 10 separately includes the image shooting unit 110 and the communication unit 120, and the position for disposing the main body section 130 is freely adjustable, a cable or the like connecting the operating table 505 to the main body section 130, for example, for power supply does not interrupt the operation of a medical staff.

3. Modifications

Some modifications of the above-described embodiment will be described. Additionally, the above-described embodiment, and each of the following modifications may be combined to the extent possible for realization.

(3-1. Modification of Connection Between Image Shooting Unit and Communication Unit)

The image shooting unit 110 and the communication unit 120 of the endoscope 10 are connected to each other by a cable or the like in the above-described embodiment to allow for wired communication (see FIG. 1). A method for connecting the image shooting unit 110 to the communication unit 120 in the endoscope 10 is not, however, limited to the example. For example, various kinds of information may be transmitted and received between the image shooting unit 110 and the communication unit 120 with no electrical contact, what is called near field communication (also referred to as near field communication (NFC) or contactless communication) in the present embodiment. Further, at that time, power may be supplied from the communication unit 120 to the image shooting unit 110 through contactless power transfer.

Figure 7:
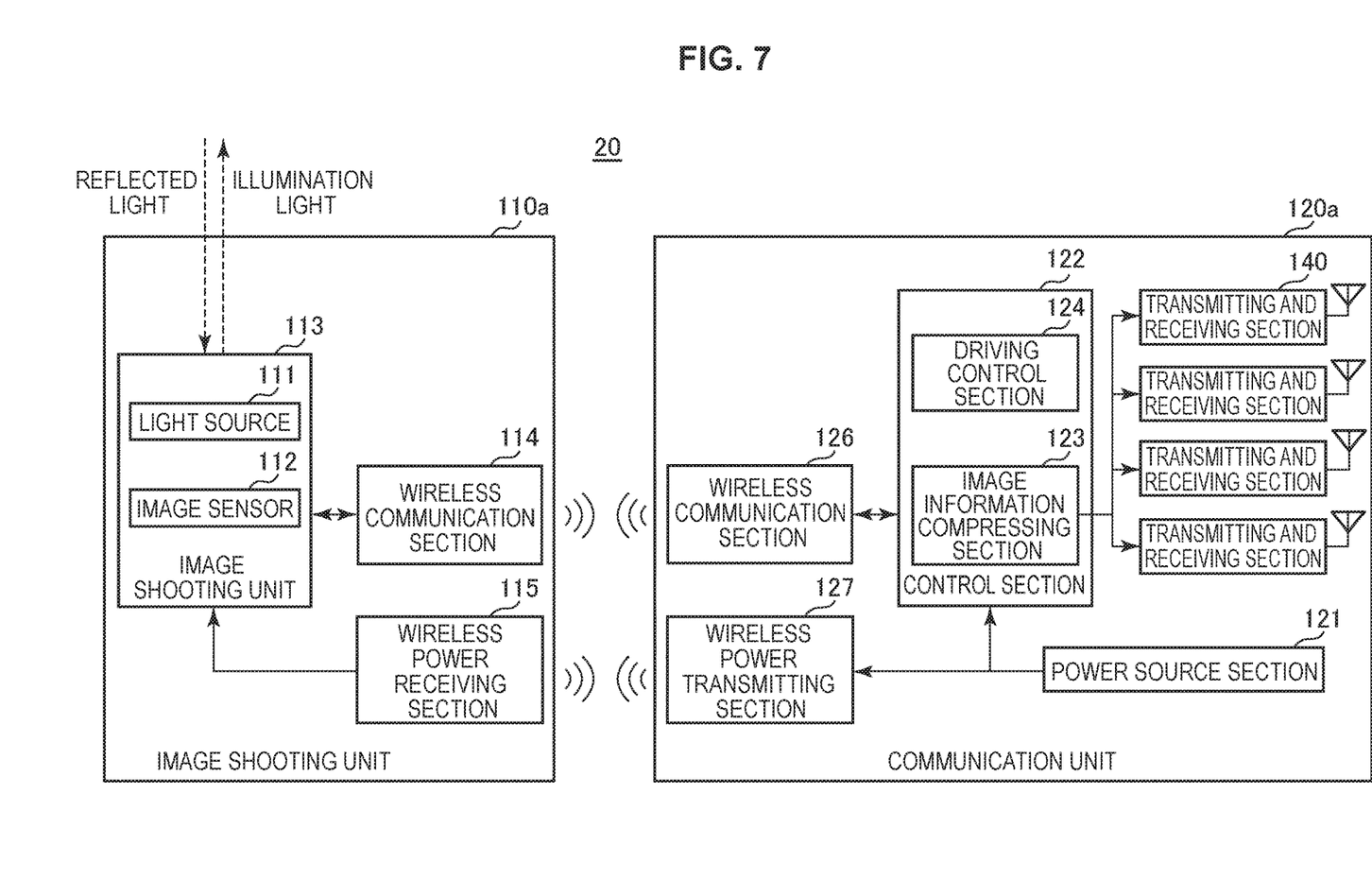
FIG. 7 is a diagram illustrating an example of a functional configuration of an endoscope according to a modification in which an image shooting unit is connected to a communication unit through near field communication.

A modification in which the image shooting unit 110 is connected to the communication unit 120 through near filed communication as described above will be described with reference to FIG. 7. FIG. 7 is a diagram illustrating an example of the functional configuration of an endoscope according to a modification in which the image shooting unit 110 is connected to the communication unit 120 through near field communication.

FIG. 7 illustrates that an endoscope 20 according to the present modification includes an image shooting unit 110a and a communication unit 120a that are connected to each other to allow for near field communication. Here, the communication unit 120a of the endoscope 20 according to the present modification also has a function of transmitting a surgical site image captured by the image shooting unit 110a to a video processor similarly to the communication unit 120 of the above-described endoscope 10 illustrated in FIG. 6. The functional configuration of the video processor is similar to the functional configuration of the video processor 30 according to the above-described embodiment, and will not be thus described in detail here. Further, FIG. 7 does not also illustrate the video processor.

The image shooting unit 110a includes an image shooting section 113, a wireless communication section 114, and a wireless power receiving section 115 as functions thereof. The image shooting section 113 captures an image of a surgical site of a patient, and acquires surgical site image information. The image shooting section 113 includes the light source 111 and the image sensor 112. Additionally, the configurations and functions of the light source 111 and the image sensor 112 are similar to the configurations and functions of these members illustrated in FIG. 6, and will not be thus described in detail here.

The driving of the image shooting section 113 is controlled under the control of the communication unit 120a. Further, the image shooting section 113 transmits the acquired surgical site image information to the communication unit 120a via the wireless communication section 114 through near field communication.

The wireless communication section 114 performs near field communication with the following wireless communication section 126 of the communication unit 120a. For example, the wireless communication section 114 includes an antenna, a control section that controls the transmission and reception of information performed via the antenna, and the like. The control section is realized by processing circuits such as a CPU, a DSP, and a GPU operating in accordance with predetermined programs.

The wireless power receiving section 115 receives power from the following wireless power transmitting section 127 of the communication unit 120a through contactless power transfer. For example, the wireless power receiving section 115 includes an antenna, a control section that controls the reception of power performed via the antenna, and the like. The control section is realized by processing circuits such as a CPU, a DSP, and a GPU operating in accordance with predetermined programs.

The communication unit 120a includes the power source section 121, the control section 122, the transmitting and receiving sections 140, the wireless communication section 126, and the wireless power transmitting section 127 as functions thereof. Further, the control section 122 includes an image information compressing section 123 and a drive control section 124 as functions thereof. Here, the functions of the power source section 121, the control section 122, and the transmitting and receiving sections 140 are similar to the functions thereof described with reference to FIG. 6, and will not be thus described in detail here.

The wireless communication section 126 performs near field communication with the wireless communication section 114 of the image shooting unit 110a. The specific configuration of the wireless communication section 126 may be similar to that of the wireless communication section 114. Additionally, a variety of existing methods, standards, or the like can be used for the specific method, communication standard, or the like of the near field communication between the image shooting unit 110a and the communication unit 120a. Accordingly, the details will not be described. For example, radio waves of a relatively high frequency band such as millimeter waves can be used for the near field communication between the image shooting unit 110a and the communication unit 120a because surgical site image information that is not compressed is exchanged therebetween.

The wireless communication section 126 receives surgical site image information transmitted from the wireless communication section 114 of the image shooting unit 110a through near field communication. The image information compressing section 123 of the control section 122 performs a compression process with little delay on the surgical site image information received by the wireless communication section 126, and the surgical site image information is transmitted to the video processor (not illustrated) via the transmitting and receiving sections 140 through wireless communication. Further, the wireless communication section 126 transmits control information from the drive control section 124 of the control section 122, such as information for controlling the driving of the image shooting section 113, or the like to the wireless communication section 114 of the image shooting unit 110a through near field communication.

The wireless power transmitting section 127 transmits power to the wireless power receiving section 115 of the image shooting unit 110a through contactless power transfer. The specific configuration of the wireless power transmitting section 127 may be similar to that of the wireless power receiving section 115. Additionally, a variety of existing methods, standards, or the like can be used for the specific method, communication standard, or the like of the contactless power transfer between the image shooting unit 110a and the communication unit 120a. Accordingly, the details will not be described.

The wireless power transmitting section 127 transmits the power stored in the power source section 121 to the wireless power receiving section 115 of the image shooting unit 110a through contactless power transfer. The power received via the wireless power receiving section 115 is supplied to the image shooting section 113, and used for driving the light source 111 and the image sensor 112 of the image shooting section 113 in the image shooting unit 110a.

Additionally, it is preferable in the present modification that the image shooting unit 110a and the communication unit 120a be disposed at particular fixed positions in an operating room at which there is no object therebetween which can obstruct the communication or the power transfer. This makes it possible to more stably transfer data through near field communication and power through contactless power transfer.

The modification in which the image shooting unit 110a is connected to the communication unit 120a through near filed communication has been described above with reference to FIG. 7. As described above, according to the present modification, the image shooting unit 110a and the communication unit 120a transmit and receive information through near field communication, and transmit and receive power through contactless power transfer. This can thus eliminate a cable between the image shooting unit 110a and the communication unit 120a, and an electrical contact such as a connector that connects the cable. The absence of a cable and an electrical contact in a clean area can eliminate a process of sterilizing these members and reduce a complicated operation of maintaining the clean area. Further, the use of near field communication and contactless power transfer allows image the shooting unit 110a and the communication unit 120a to perform communication and to transfer power, for example, even in a case where there is a barrier such as vinyl therebetween to separate a clean area and an unclean area. It is therefore easier to maintain the clean area.

(3-2. Modification of Position for Disposing Transmitting and Receiving Section of Communication Unit)

The transmitting and receiving sections 140 (antennas) of the communication unit 120 of the endoscope 10 are disposed at the four corners of the operating table 505 (see FIG.

2) in the above-described embodiment. The positions for disposing the transmitting and receiving sections 140 and the number of transmitting and receiving sections 140 to be disposed are not, however, limited to the example. The transmitting and receiving sections 140 may be disposed at any positions in the present embodiment as long as the transmitting and receiving sections 140 are disposed at positions at which the transmission of radio waves from the transmitting and receiving sections 140 to the video processor 30 is difficult to block.

Figure 8:
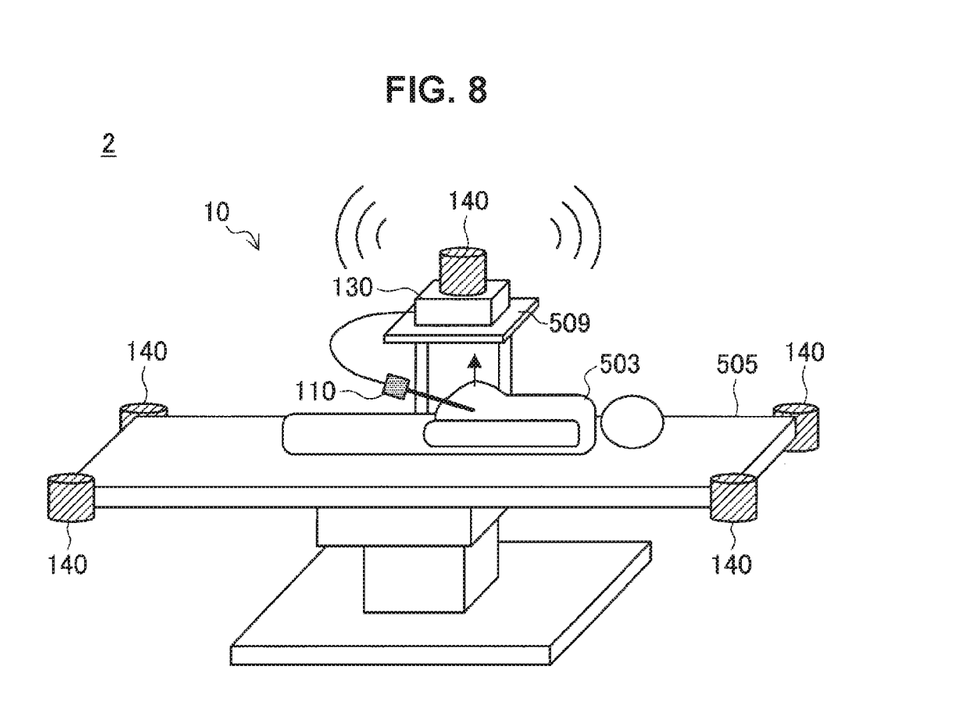
FIG. 8 is an explanatory diagram for describing a modification in which a transmitting and receiving section of a communication unit of an endoscope is disposed in another place.

A modification in which the transmitting and receiving sections 140 of the communication unit 120 of the endoscope 10 are disposed in another place will be described with reference to FIG. 8. FIG. 8 is an explanatory diagram for describing the modification in which the transmitting and receiving sections 140 of the communication unit 120 of the endoscope 10 are disposed in another place. Additionally, an observation system according to the present modification is different from the above-described observation system 1 illustrated in FIG. 2 in that the transmitting and receiving sections 140 are disposed at different positions. The following description of the present modification will not thus describe in detail what is similar to that of the above-described embodiment, but differences from the above-described embodiment will be chiefly described.

FIG. 8 illustrates that an observation system 2 according to the present modification is applied to the patient 503 on the operating table 505. FIG. 8 illustrates only the endoscope 10 among devices included in the observation system 2. Although not illustrated, the observation system 2 according to the present modification also includes a video processor provided in an operating room similarly to the above-described observation system 1, and a surgical site image captured by the endoscope 10 is transmitted to the video processor. The functional configuration of the video processor is similar to the functional configuration of the video processor 30 according to the above-described embodiment, and will not be thus described in detail here.

Here, examples of operative procedures include a lift method. An instrument referred to as a retractor is installed over a patient, and the retractor lifts a part of the body of the patient during an operation in the lift method. FIG. 8 illustrates an operation performed in the lift method.

As illustrated in FIG. 8, the transmitting and receiving section 140 of the communication unit 120 is installed on a retractor 509 in addition to the four corners of the operating table 505 in the present modification. Further, the main body section 130 of the communication unit 120 is also installed on the retractor 509. Disposing the transmitting and receiving section 140 at a relatively high position such as a position on the retractor 509 makes it more difficult to block the radio waves emitted from the transmitting and receiving section 140. Accordingly, the stability of the communication is strengthened.

Additionally, the position for disposing the transmitting and receiving section 140 is not limited to the position on the retractor 509. In a case where another instrument is installed over a patient in accordance with an operative procedure, the transmitting and receiving section 140 may be disposed as appropriate on the other instrument.

Further, the main body section 130 is disposed on the retractor 509 along with the transmitting and receiving section 140 in the illustrated example. The position for disposing the main body section 130 is not, however, limited to the example. The main body section 130 may be disposed at any position. Even in a case where the transmitting and receiving section 140 is disposed on the retractor 509, the main body section 130 may be disposed at any position such as the bottom of the operating table 505 as illustrated, for example, in FIGS. 3 to 5.

The modification in which the transmitting and receiving sections 140 of the communication unit 120 of the endoscope 10 disposed in another place has been described above with reference to FIG. 8. As described above, according to the present modification, disposing the transmitting and receiving section 140 at a relatively high position makes it more difficult to block the radio waves emitted from the transmitting and receiving section 140. Accordingly, it is possible to more stably transmit a surgical site image to the video processor.

4. Supplemental Information

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An observation device including:

an image shooting unit composed of a first housing and configured to capture an image of a surgical site of a patient; and a communication unit composed of a second housing disposed away from the first housing, and configured to wirelessly transmit, to an external device, image information on the surgical site the image of which is captured by the image shooting unit.

(2)

The observation device according to (1), wherein the image information is transmitted between the image shooting unit and the communication unit through wired communication.

(3)

The observation device according to (1), wherein the image information is transmitted between the image shooting unit and the communication unit through near field communication.

(4)

The observation device according to any one of (1) to (3), wherein the communication unit includes a driving control section configured to control driving of the image shooting unit.

(5)

The observation device according to any one of (1) to (4), wherein the communication unit includes an image information compressing section configured to perform a compression process on the image information.

(6)
The observation device according to (5), wherein
the communication unit further includes a power source section configured to supply power at least to the image information compressing section.
(7)
The observation device according to (6), wherein
the power source section also supplies power to the image shooting unit.
(8)
The observation device according to any one of (1) to (7), wherein
the communication unit includes a main body section and an antenna that are connected to each other to allow for wired communication, the main body section at least controlling transmission of the image information to the external device, the antenna transmitting the image information to the external device.
(9)
The observation device according to (8), wherein
the main body section is disposed at an operating table that supports the patient.
(10)
The observation device according to (8) or (9), wherein
the antenna is disposed at at least one of four corners of a bed that supports the patient.
(11)
The observation device according to any one of (8) to (9), wherein
the antenna is disposed on an instrument provided over a body of the patient.
(12)
The observation device according to any one of (1) to (11), wherein
the observation device is an endoscope, and
the image shooting unit includes a lens barrel, and a light source and an image sensor provided in the lens barrel.
(13)
An observation system including:
an observation device configured to wirelessly transmit image information on a surgical site of a patient; and
a display control device configured to receive the image information transmitted from the observation device, and to control display of an image on the surgical site, wherein
the observation device includes an image shooting unit composed of a first housing and configured to capture an image of the surgical site of the patient, and a communication unit composed of a second housing disposed away from the first housing, and configured to wirelessly transmit, to the display control device, the image information on the surgical site the image of which is captured by the image shooting unit.

REFERENCE SIGNS LIST 1, 2 observation system
10, 20 endoscope (observation device)
30 video processor (display control device)
110, 110a image shooting unit
111 light source
112 image sensor
113 image shooting section
120, 120a communication unit
121 power source section
122 control section
123 image information compressing section
130 main body section
140 transmitting and receiving section
301 transmitting and receiving section
302 control section
303 image information decompressing section

The invention claimed is:
1. An observation device, comprising:
an image shooting device that comprises a first housing, wherein the image shooting device is configured to capture an image of a surgical site of a patient; and
a communication device that comprises:
a main body, wherein the main body comprises at least one processor in a second housing, wherein the second housing is separated from the first housing; and
a plurality of antennas configured to wirelessly transmit, to an external device, image information on the surgical site based on the captured image of the surgical site, wherein
the image information is transmitted between the image shooting device and the communication device through wired communication,
the second housing of the main body is separated and spaced apart from a first antenna of the plurality of antennas,
the first antenna is on an operating table,
a second antenna of the plurality of antennas is at a position of the second housing, wherein the position of the second housing is different from a position of the first antenna, and
the main body is connected to the plurality of antennas via cables.
2. The observation device according to claim 1, wherein the image information is transmitted between the image shooting device and the communication device through near field communication.
3. The observation device according to claim 1, wherein the at least one processor of the communication device is configured to control driving of the image shooting device.
4. The observation device according to claim 1, wherein the at least one processor is further configured to execute a compression process on the image information.
5. The observation device according to claim 4, wherein the communication device further includes a power source configured to supply power to the at least one processor for the execution of the compression process.
6. The observation device according to claim 5, wherein the power source supplies the power to the image shooting device.
7. The observation device according to claim 1, wherein
the main body is connected to the first antenna to allow for wired communication,
the main body is configured to control transmission of the image information to the external device, and
the first antenna is configured to transmit the image information to the external device.
8. The observation device according to claim 7, wherein the main body is on an instrument provided over a body of the patient.
9. The observation device according to claim 7, wherein the first antenna is at at least one of four corners of the operating table that supports the patient.
10. The observation device according to claim 7, wherein the second antenna is on an instrument provided over a body of the patient.
11. The observation device according to claim 1, wherein
the observation device is an endoscope,
the image shooting device includes a lens barrel, and
the lens barrel comprises a light source and an image sensor.

12. The observation device according to claim 11, wherein the at least one processor is further configured to control an analog gain of the image sensor to control driving of the light source.

13. An observation system, comprising:
- an observation device configured to wirelessly transmit image information on a surgical site of a patient; and
- a display control device configured to:
  - receive the image information transmitted from the observation device; and
  - control display of an image of the surgical site,
- wherein the observation device includes:
  - an image shooting device that comprises a first housing, wherein the image shooting device is configured to capture the image of the surgical site of the patient; and
  - a communication device that comprises:
    - a main body, wherein
      - the main body comprises at least one processor in a second housing,
      - the second housing is separated from the first housing, and
      - the image information is transmitted between the image shooting device and the communication device through wired communication; and
    - a plurality of antennas configured to wirelessly transmit, to the display control device, the image information on the surgical site based on the captured image of the surgical site, wherein
      - the second housing of the main body is separated and spaced apart from a first antenna of the plurality of antennas,
      - the first antenna is on an operating table,
      - a second antenna of the plurality of antennas is at a position of the second housing, wherein the position of the second housing is different from a position of the first antenna, and
      - the main body is connected to the plurality of antennas via cables.

\* \* \* \* \*